United States Patent
Tittel et al.

(10) Patent No.: US 6,831,748 B2
(45) Date of Patent: Dec. 14, 2004

(54) PLASMON RESONANCE SENSOR, ESPECIALLY FOR USE IN BIOSENSOR TECHNOLOGY

(75) Inventors: Jakob Tittel, Gauting (DE); Carsten Luethy, Munich (DE)

(73) Assignee: Jandratek GmbH, Wallenfels (DE)

( * ) Notice: Subject to any disclaimer, the term of this patent is extended or adjusted under 35 U.S.C. 154(b) by 0 days.

(21) Appl. No.: 10/416,145

(22) PCT Filed: Nov. 8, 2001

(86) PCT No.: PCT/EP01/12932
§ 371 (c)(1),
(2), (4) Date: Dec. 22, 2003

(87) PCT Pub. No.: WO02/39095
PCT Pub. Date: May 16, 2002

(65) Prior Publication Data
US 2004/0090630 A1 May 13, 2004

(30) Foreign Application Priority Data
Nov. 10, 2000 (DE) ......................................... 100 55 655

(51) Int. Cl.[7] .............................................. G01N 21/55
(52) U.S. Cl. .................................................... 356/445
(58) Field of Search ........................ 356/128, 134–136, 356/317, 318, 445

(56) References Cited

U.S. PATENT DOCUMENTS 4,844,613 A    7/1989   Batchelder et al.
5,485,277 A *  1/1996   Foster ........................ 356/445
5,822,073 A * 10/1998   Yee et al. .................... 356/445
5,991,048 A * 11/1999   Karlson et al. .............. 356/445
6,424,418 B2 *  7/2002   Kawabata et al. ........... 356/445
6,466,323 B1 * 10/2002   Anderson et al. ........... 356/445
6,570,657 B1    5/2003   Hoppe et al.
2001/0040679 A1 11/2001   Sakuranaga et al.

FOREIGN PATENT DOCUMENTS

| DE | 198 14 811 C1 | 8/1999 |
| EP | 0 305 109 B1 | 7/1993 |
| WO | WO 9522754 A1 * | 8/1995 .......... G01N/21/03 |
| WO | 96/02823 | 2/1996 |
| WO | 96/22754 | 8/1996 |

OTHER PUBLICATIONS

Patent Abstracts of Japan JP 11344437 of Dec. 14, 1999.

* cited by examiner

Primary Examiner—Zandra V. Smith
Assistant Examiner—Gordon J. Stock, Jr.
(74) Attorney, Agent, or Firm—Michael J. Striker

(57) ABSTRACT

A plasmon resonance sensor has an optically transparent body, a reflective layer on its one face and having a surface sensitive to molecules, a light source for emitting a divergent light through the body onto an inner face of the layer, and a detector assigned to an emerging beam path reflected by the layer and registering an angle of incidence of the light changing as a result of molecule buildups, wherein the light source is assigned a non-pointlike emission face with an extent of at least 10 µm, and a collimation lens is arranged in the emerging beam path between the optically transparent body and the detector.

14 Claims, 3 Drawing Sheets

PLASMON RESONANCE SENSOR, ESPECIALLY FOR USE IN BIOSENSOR TECHNOLOGY

BACKGROUND OF THE INVENTION

The invention relates to a plasmon resonance sensor, in particular for biosensor technology, with an optically transparent body, in particular a glass prism, a reflective metal layer or semiconductor layer which is applied to one face of the body and has a surface sensitive to molecules to be detected, which forms a measurement cell in conjunction with a cuvette, a light source for emitting a divergent light pencil or beam path through the optically transparent body onto the inner face of the layer, and a detector which is assigned to the emerging beam path reflected by the layer and registers as a function of time the angle of incidence of the light, which changes as a result of molecule buildups on the sensitive surface, at which an intensity minimum of emerging light occurs owing to resonance.

Such a plasmon resonance sensor, with a glass prism and a gold layer, is known from U.S. Pat. No. 4,844,613. The light source used there is a laser diode, which emits in a pointlike fashion with an angle range which directly covers all the angles of incidence relevant to resonance detection.

For plasmon resonance determination, in simple terms, the intensity of the light reflected by the gold layer is detected. In order to find the resonance, either the angle of incidence of the light on the gold layer is scanned at a constant wavelength, or the wavelength is scanned at a constant angle of incidence. Surface plasmon resonance is identified by reduced reflectivity with a particular combination of angle of incidence and wavelength of the light. From the position of the resonance condition, it is possible to determine the refractive index of the layer, for example of a sample liquid, located on the gold layer. The interaction range, starting from the gold layer and extending into the layer to be determined, is restricted to a thickness of about one wavelength of the light.

In order to obtain the best possible resolution, either monochromatic light or a very accurately defined angle of incidence is necessary. WO 96 02 823 proposes the use of a monochromatic light source, the angle of incidence being scanned using a rotating mirror. However, moving parts are necessary to do this, which is found to be a disadvantage. Conversely, according to EP 305 109 B1, the corresponding angle range is generated optically by a beam fan. In both embodiments, the place of the reflection on the gold layer is very accurately localized. This can lead to undesirable heating of the gold layer, because the energy of the plasmons which are generated is dissipated in the gold layer. The refractive index of liquids, the medium most commonly to be measured in biosensors, depends strongly on temperature, so that falsifications of the measurement may arise because of the heating. The accurate localization of the reflection on the gold layer furthermore leads to problems in terms of measurement accuracy in the event of even very minor inhomogeneities of the gold layer, for example the small holes (pinholes) which are generated during thermal evaporation coating of gold layers.

SUMMARY OF THE INVENTION

The problem of the gold layer being heated is circumvented by the plasmon resonance sensor described in the introduction. There is no focus on the gold layer owing to the divergently incident light, but instead the various angles of incidence are each reflected at a different point on the gold layer. This avoids heating of the gold layer. However, the problem due to inhomogeneities in the gold layer is exacerbated here because different angles of incidence are influenced varyingly by them. The physical size of the laser diodes used as a light source may furthermore be a hindrance, because miniaturization and parallelization of the measurement channels is of crucial importance in modern instruments. Lastly, it is also to be regarded as disadvantageous that a point light source, namely a laser diode, needs to be used in the interest of good resolution. A light-emitting diode, which typically has an emission face with a diameter of 150 $\mu$m, cannot be used because of its extended emission and also because of the polychromatic emission.

It is an object of the invention to improve the plasmon resonance sensor described in the introduction, in such a way that the effect of inhomogeneities of the metal layer is suppressed while maintaining the simple design and substantial freedom from heating of the gold layer, and exact measurement results are therefore achieved.

This object is achieved according to the invention by the fact that the light source is assigned a non-pointlike emission face with an extent of at least 10 $\mu$m, and that a collimation lens is arranged in the emerging beam path between the optically transparent body and the detector.

The invention hence operates with a spatially extended light source, or emission face. This leads to an inherently undesirable significant broadening of the detected plasmon, because the angle information becomes blurred owing to the spatial extent of the light source, which can be regarded as a multiplicity of point light sources in spatial proximity. This apparently disadvantageous result is nevertheless compensated for according to the invention by the collimation optics which are provided.

Since the spatially extended light source which is used corresponds to a multiplicity of conically emitting point light sources in close proximity, light beams with the same angle of incidence strike the gold layer at different points, or over a wide region. Put another way, a plurality of different angles of incidence will be encountered at one place on the gold layer. The same angles of incidence of different places on the gold layer are then sent, having been recombined by the collimation lens provided according to the invention, to the detector where they are detected. This affords the substantial advantage that averaging takes place over a wide region of the gold layer during measurement of the plasmon generation, so that inhomogeneities of the gold layer now become unimportant, or almost so.

Expediently, the emission face is arranged at one focal point and the illuminated face of the detector is arranged at the other focal point of the collimation lens. Such a design fully compensates for the aforementioned broadening affect due to the extended emission face. Concerning the focal position of the emission face, it should in this case be borne in mind that the beam path is refracted in the prism, so that the focal position may need to be corrected.

In a particularly advantageous embodiment, the emission face is formed by the end of an optical fiber next to the optically transparent body. Optical fibers provide the opportunity to deliver the light close up to the glass body in a straightforward way, in which case the light source itself may be arranged some distance away, which offers design advantages and favors the aforementioned miniaturization. It was not previously possible to use optical fibers, or it was possible to use them only with great restrictions, because they do not have the emission face which is pointlike owing to the desired resolution. Although there are optical fibers with very small core diameters, namely single-mode fibers with a core diameter of from 2 to 9 µm, these are not in fact true point light sources and, in particular, they are difficult to work with. Elaborate input optics in conjunction with a separate light source for each individual optical fiber are needed. Technical implementation is therefore difficult and expensive. The same correspondingly applies to multi-mode fibers with a core diameter of from 50 to 150 µm.

To carry out the invention using optical fibers, ones with core diameters in the range of from 300 to 700 µm are therefore preferred, because the invention allows their use and correspondingly thick optical fibers are much easier to work with, especially in terms of light input. For example, the light from a single light source may be put into a plurality of such thick optical fibers. To this end, although the light is collimated so that the beam illuminates all the fibers, it is nevertheless not focused onto a single fiber, as is required for single-mode fibers. It has moreover been found that an emission face with an extent in the aforementioned range of from 300 to 700 µm leads to good measurement results, irrespective of the use of optical fibers.

Further expedient refinements of the invention are given in the dependent claims.

BRIEF DESCRIPTION OF THE DRAWINGS

Exemplary embodiments of the invention will be explained in more detail below with reference to a schematic drawing, in which.

DETAILED DESCRIPTION OF THE PREFERRED EMBODIMENTS

Figure 1:
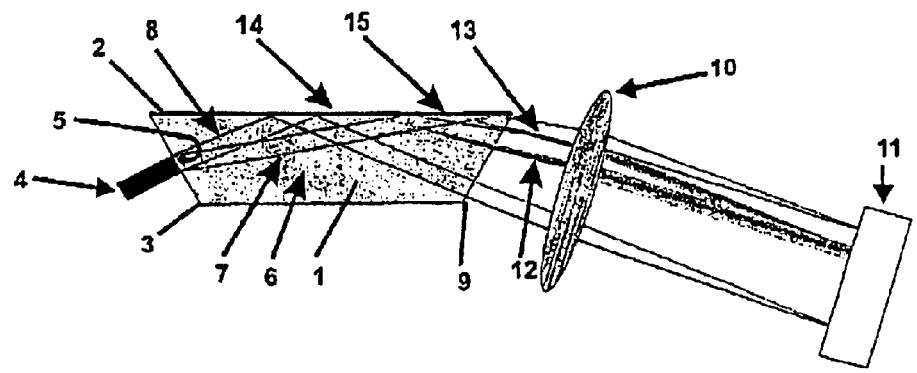
FIG. 1 shows a plasmon resonance sensor with thick optical fibers adjoining the prism in side view, with indication of the light-beam pencils coming from the two outlying points on the emission face and the respectively associated emergent beam attenuated by plasmon resonance.

According to FIG. 1, a glass prism 1 of trapezoidal cross section is provided, to which a gold layer 2 is applied, for example by evaporation coating. This gold layer 2, which is for example 50 nm thick, carries a sensitive coating on the outside, on which the biomolecules to be detected in a sample to be studied can accumulate. Such sensitive coatings and their regeneration are familiar to the person skilled in the art.

An optical fiber 4 having a thick core diameter of, for example, 500 µm with a correspondingly extended—non-pointlike—emission face 5 is connected to the light incidence side 3 of the glass prism 1. Light is fed into the opposite end of the optical fiber 4 from the emission face 5, in a manner which is not shown, by means of a light-emitting diode or another light source.

A light-beam pencil 6, which is bounded by the two indicated edge beam pencils 7 and 8, is emitted by the emission face 5. The light-beam pencil 6 is reflected by the gold layer 2, emerges through the light exit side 9 of the glass prism 1 and is directed by a collimation lens 10 onto a detector 11. This spatially resolving detector 11 is formed by a CCD sensor (CCD chip) and is provided with an polariser in front of it (p polarization).

The collimation lens 10 and the detector 11 are placed in the scope of a confocal arrangement so that the emission face 5 is arranged at one focal point of the collimation lens 10 and the imaging face of the detector 11 is arranged at the other focal point. This confocal arrangement can be seen in particular from the representation in FIG. 4, where the focal lengths f and f' of the collimation lens are indicated.

In FIG. 1, as well as in the other figures, the beam path of the light-beam pencil 6 is represented with neglect of the beam refraction at the glass/air transition. The respective attenuated-intensity emerging light beams 12 and 13 are furthermore represented for the two edge-beam pencils 7 and 8, which belong to the angle of incidence which is influenced by the plasmon resonance. In this case, it is characteristic of the invention that these attenuated light beams 12 and 13 emerge from various points 14 and 15 on the gold layer 2, corresponding to the extent of the emission face 5, but are sent in combination onto the detector face by the action of the collimation lens 10, so that a precise measurement signal is obtained which accurately characterizes the relevant angle of incidence. The result of this is a good angular resolution and, in spite of this, the advantage that the region of the plasmon generation on the gold layer 2 is extended because it does not lie in the focal plane of the collimation lens 10. Averaging therefore takes place over a wide region of the gold layer, so that local inhomogeneities that affect the surface plasmon resonance are averaged out.

These circumstances accordingly apply even if operation is carried out with an emission face which is less extended but can nevertheless be regarded as two-dimensional and not as pointlike. For instance, according to FIG. 2, the glass prism 1 with the gold layer 2 may also be assigned a special laser diode 16 which emits with an extent of at least 10 µm, instead of the optical fiber 4. Since in this case the emission face appears pointlike in the drawing according to FIG. 2, in spite of its extended nature, it is not possible to draw in different beam pencils with the same angle of incidence.

Figure 2:
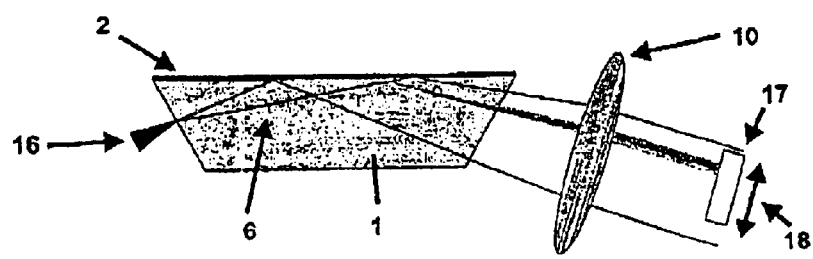
FIG. 2 shows a representation corresponding to FIG. 1 using a laser diode without an optical fiber and with a detector that can be adjusted to the plasmon resonance range.

FIG. 2 furthermore represents a comparatively small detector 17, which can be displaced according to the double arrow 18 and can be adjusted to the range of the emerging light beams attenuated by the plasmon resonance.

Figure 3:
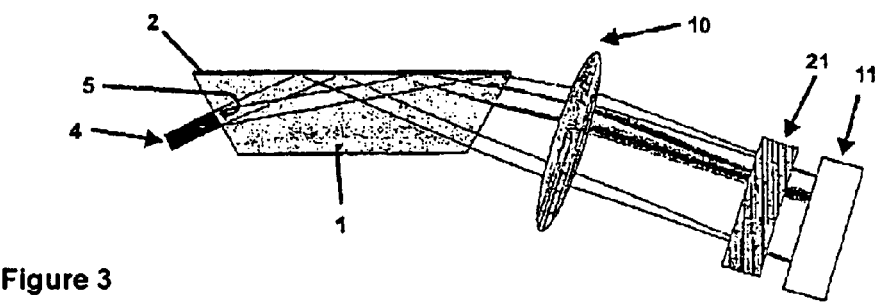
FIG. 3 shows a side view corresponding to FIG. 1 of a plasmon resonance sensor intended for a plurality of parallel measurement cells, with an additional cylindrical lens.
Figure 4:
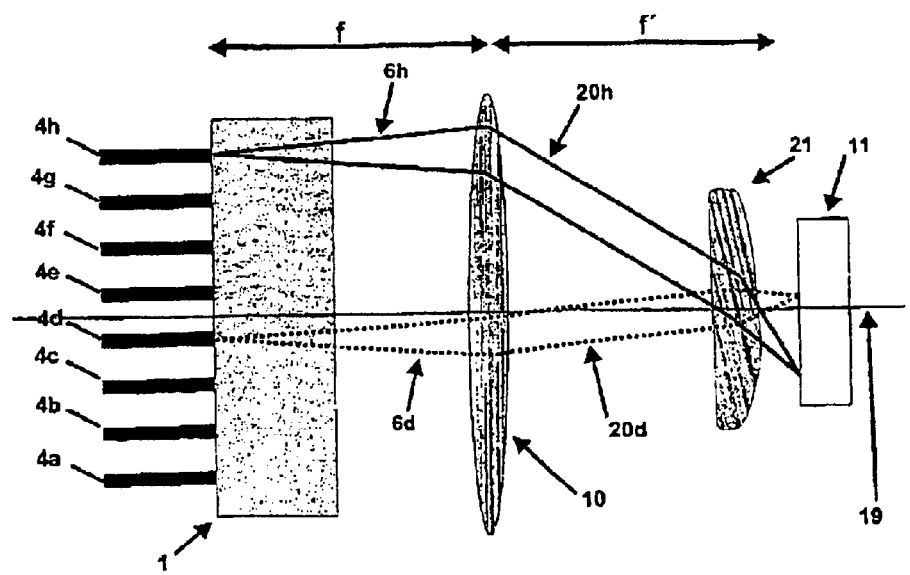
FIG. 4 shows a plan view, represented on a modified scale, of the embodiment according to FIG. 3 while illustrating the beam paths coming from an outlying optical fiber and from a central optical fiber in the plane of the drawing.

The embodiment according to FIGS. 3 and 4 is intended for the arrangement of eight parallel measurement cells on the gold layer 2, as can be inferred from FIG. 4 with the eight parallel optical fibers 4a to 4h, each of which is assigned to a separate measurement cell. Owing to the substantial similarity with the embodiment according to FIG. 1, FIGS. 3 and 4 use the same reference numerals as FIG. 1. The relevant description will therefore not be repeated, and this also applies to the corresponding beam path according to FIG. 3.

As can be seen from FIG. 4, the glass prism 1 is elongate and the eight optical fibers 4a to 4h are arranged uniformly distributed over its length. Their emission faces are arranged in the focal plane with the focal length distance f, while the detector 11 with its detector face (imaging face) is arranged in the other focal plane with the focal point distance f'.

For the optical fibers 4a to 4h, FIG. 4 indicates the light-beam pencils 6d and 6h which diverge in a direction transverse to the optical axis 19, or the incidence plane passing through this axis normal to the gold layer 2, as far as the collimation lens 10 where they have a width corresponding approximately to the distance between neighboring optical fibers 4a to 4h, before being deviated in the form of parallel beam pencils 20d and 20h, respectively. By a cylindrical lens 21 arranged in front of the detector 11 in the beam path, all the beam pencils 20 are focused perpendicularly to the optical axis 19, or the incidence plane, onto the detector 11. The individual beam pencils 6 and 20 are therefore imaged on the detector 11 in the form of mutually parallel light strips.

Figure 5:
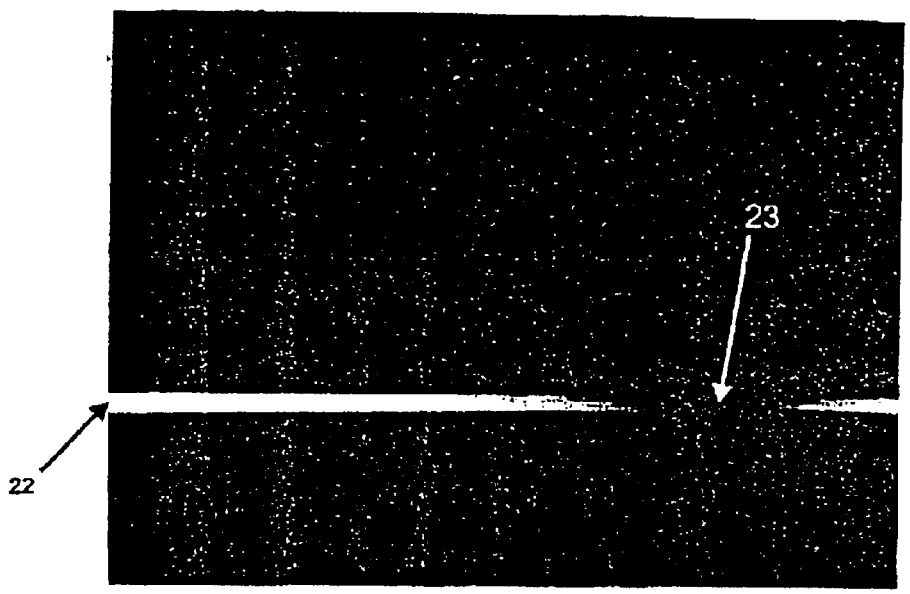
FIG. 5 shows the measured detector signal which comes from one of the eight optical fibers provided according to FIG. 4.

FIG. 5 shows—in a horizontal direction differing from FIG. 4—such a light strip 22 as a measured detector signal of one of the eight light sources or optical fibers 4a to 4h. The place 23 of reduced light intensity, at which the light signal is attenuated owing to the plasmon resonance (colored black) can be seen clearly within this light strip 22.

Figure 6:
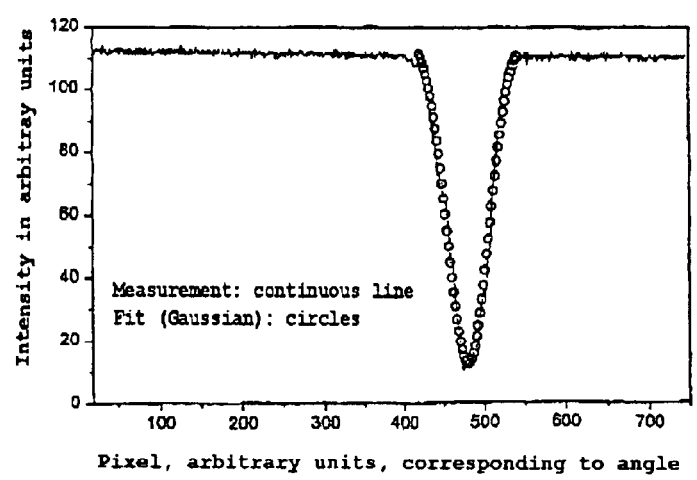
FIG. 6 shows a graphical representation of the measured light intensities corresponding to FIG. 5.

The associated intensity measurement is graphically depicted in FIG. 6, where the intensity of the light incident on the detector 11 is plotted against the measurement range corresponding to the length of the light strip 22. This length range is scaled from 0 to 750 units, the various values corresponding to particular angles of incidence. As the graph shows, in a range of about 100 units, there is a reduction in the otherwise constantly measured intensity by a clear 110 units with a pronounced intensity minimum at the angle of incidence corresponding to 480 units, where the normal intensity is reduced by about 90% owing to the plasmon resonance.

What is claimed is:

1. A plasmon resonance sensor, comprising:
    an optically transparent body (1);
    a reflective metal layer (2) or semiconductor layer, wherein said reflective metal layer or semiconductor layer is applied to one face of the body (1) and has a surface sensitive to molecules to be detected, thereby forming a measurement cell in conjunction with a cuvette;
    a light source for emitting a divergent light pencil or beam path (6) through the optically transparent body (1) onto an inner face of the layer (2); and
    a detector (11, 17), wherein the detector is assigned to the emerging beam path reflected by the layer (2) and registers as a function of time an angle of incidence of the light, wherein the angle of incidence of light changes as a result of molecule buildups on the sensitive surface, wherein an intensity minimum of emerging light occurs owing to resonance, wherein the light source is assigned a non-pointlike emission face (5) with an extent of at least 10 $\mu$m, and wherein a collimation lens (10) is arranged in the emerging beam path between the optically transparent body (1) and the detector (11, 17).

2. The plasmon resonance sensor as defined in claim 1, wherein the emission face (5) is arranged at one focal point (distance f) and the illuminated face of the detector (11, 17) is arranged at the other focal point (distance f) of the collimation lens (10).

3. The plasmon resonance sensor as defined in claim 1, wherein the emission face (5) has an extent of between 300 and 700 $\mu$m.

4. The plasmon resonance sensor as defined in claim 1, wherein a laser diode (16) is provided as the light source.

5. The plasmon resonance sensor as defined in claim 1, wherein a spatially resolving detector is provided in the form of a CCD sensor.

6. The plasmon resonance sensor as defined in claim 1, wherein the sensor is used for biosensor technology.

7. The plasmon resonance sensor as defined in claim 1, wherein the optically transparent body (1) is a glass prism.

8. The plasmon resonance sensor as defined in claim 1, wherein the emission face (5) is formed by the end of an optical fiber (4) next to the optically transparent body (1).

9. The plasmon resonance sensor as defined in claim 8, wherein a light-emitting diode is provided for feeding the light into the optical fiber (4).

10. The plasmon resonance sensor as defined claim 1, wherein having two or more measurement cells are assigned to the optically transparent body (1), wherein a separate emission face (5) is provided for each measurement cell.

11. The plasmon resonance sensor as defined in claim 10, wherein each measurement cell is assigned a separate optical fiber (4a to 4h) with the emission face (5).

12. The plasmon resonance sensor as defined in claim 11, wherein a plurality of optical fibers (4a to 4h) are assigned to a common light source.

13. The plasmon resonance sensor as defined in claim 10, wherein a cylindrical lens (21), is additionally provided in front of the detector (11) in the emerging beam path, wherein the cylindrical lens focuses the beam path perpendicularly onto the detector (11) with respect to an incidence plane.

14. The plasmon resonance sensor as defined in claim 13, wherein the cylindrical lens (21) is arranged between the collimation lens (10) and the detector (11).

* * * * *